United States Patent [19]

Hass

[11] Patent Number: 4,659,713

[45] Date of Patent: Apr. 21, 1987

[54] QUINOXALINEDIONE COMPOUNDS USEFUL FOR CONTROLLING COCCIDIOSIS

[75] Inventor: D. Kendall Hass, Modesto, Calif.

[73] Assignee: International Minerals & Chemical Corp., Terre Haute, Ind.

[21] Appl. No.: 656,391

[22] Filed: Oct. 1, 1984

[51] Int. Cl.$^4$ ............................................. A61K 31/50
[52] U.S. Cl. .................................................... 514/249
[58] Field of Search ........................ 514/249; 544/354

[56] References Cited

U.S. PATENT DOCUMENTS

| | | | |
|---|---|---|---|
| 3,186,905 | 6/1965 | Hattori et al. | 514/249 |
| 3,250,774 | 5/1966 | Schmidt et al. | 544/354 |
| 3,845,047 | 10/1974 | Egli et al. | 260/250 |
| 3,992,378 | 11/1976 | St. Clair | 260/250 Q |

OTHER PUBLICATIONS

Derwent, 50585.
Derwent, 6816.
Huntress et al, JACS, pp. 2644–2649, 1942.

*Primary Examiner*—Frederick E. Waddell
*Attorney, Agent, or Firm*—Thomas L. Farquer; Robert H. Dewey

[57] ABSTRACT

Quinoxalinedione compounds are effective coccidiostats when administered to animals. The compounds are conveniently incorporated into standard animal feeds. The compounds are particularly effective for controlling coccidiosis in poultry.

9 Claims, No Drawings

QUINOXALINEDIONE COMPOUNDS USEFUL FOR CONTROLLING COCCIDIOSIS

BACKGROUND OF INVENTION

The present invention relates to quinoxalinedione compounds useful for the control of coccidiosis in animals.

U.S. Pat. No. 3,992,378 discloses quinoxalinedione compounds useful as hypnotic agents. In particular, 7-chloro-5-nitro-2(1H),3(4H)-quinoxalinedione; 5-nitro-7-trifluoromethyl-2(1H),3(4H)-quinoxalinedione; and 5-nitro-2(1H)-quinoxalinedione are disclosed.

Heretofore, the present quinoxalinedione compounds have not been disclosed as being effective for the control of coccidiosis.

SUMMARY OF THE INVENTION

Briefly, in accordance with the present invention, coccidiosis is controlled in animals by administering to animals an effective coccidiosis-controlling amount of a 5-nitro-2(1H),3(4H)-quinoxalinedione compound or a tautomer or a physiologically acceptable salt thereof (hereinafter referred to as "the present quinoxalinedione compounds"). Mixtures of these compounds can also be used.

Additionally, the present invention relates to animal feed compositions containing a nutritional animal feed and one or more of the present quinoxalinedione compounds.

Of particular interest in the practice of the present invention is a method of controlling coccidiosis in poultry by the oral administration to poultry of an effective coccidiosis controlling amount of 7-chloro-5-nitro-2(1H),3(4H)-quinoxalinedione or a salt or tautomer thereof. This compound is typically administered as a component in the poultry feed.

DETAILED DESCRIPTION OF THE INVENTION

The term "controlling coccidiosis", when used herein, refers to the use of the present quinoxalinedione compounds as prophylactic agents in the prevention of coccidiosis in animals as well as their use as therapeutic agents in treating active coccidial infections in animals. The term "animals" includes birds and mammals. Preferred animals include poultry.

The present quinoxalinedione compounds are known compounds and are disclosed in U.S. Pat. No. 3,992,378 which is incorporated herein by reference. This U.S. Patent also teaches methods of preparing the present quinoxalinedione compounds and starting materials used in their preparation. The present quinoxalinedione compounds correspond to the formula:

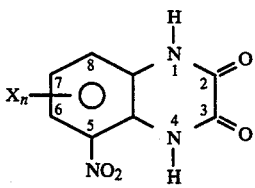

wherein
X represents H, Cl, Br, F, I, CCl$_3$, CCl$_2$F, CHF$_2$ or CF$_3$; n represents 1 or 2; and
tautomers and physiologically acceptable salts thereof. Preferred compounds include those wherein X is in the 7-ring position which correspond to the formula:

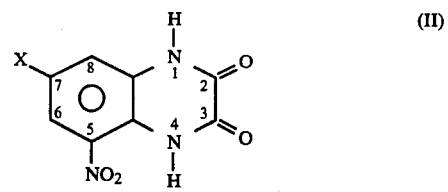

wherein
X represents H, Cl, Br, F, I, CCl$_3$, CCl$_2$F, CClF$_2$, CHF$_2$ or CF$_3$; and
tautomers and physiologically acceptable salts thereof. Especially preferred compounds are those wherein X is Cl.

The present quinoxalinedione compounds are prepared in accordance with conventional procedures. Advantageously, an appropriately substituted o-phenylenediamine is condensed with diethyl oxalate at temperatures between about 50° C. and 100° C. and preferably at reflux temperatures. These reactions are characterized as follows:

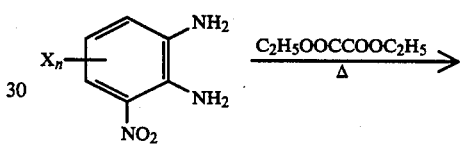

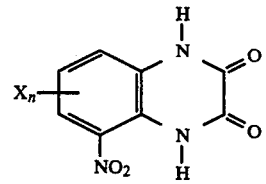

wherein X and n is as described hereinbefore. An inert liquid can be employed as a reaction medium but diethyl oxalate, a liquid, is preferably employed in excess to serve as the reaction medium. Typically, the product precipitates in the reaction mixture. The product is separated and purified employing standard separatory and purification techniques.

In practicing the present invention, any one or more of the compounds of Formula I are administered to animals in an effective coccidiosis-controlling amount. Although the route of administration is not critical, it is preferred to administer the present quinoxalinedione compounds orally to animals in a dosage form, such as, in admixture with feed, as a component of the water supply, feed concentrate or supplements and additionally in the form of boluses, capsules, tablets, suspensions, emulsions or solutions containing one or more of said compounds. These dosage forms are themselves novel and constitute an embodiment of the invention.

The effective coccidiosis-controlling amounts of the present quinoxalinedione compounds are usually found in the range of from about 0.1 to about 100 milligrams per kilogram of body weight of the animal per day (mg/kg/day). This effective range can vary depending on many factors, such as, the size of the animal, the species of the animal, the age of the animal, the particular active compound used, the dosage form employed or the particular sensitivity of the particular animal. The optimum range of an effective amount, based on variables such as those mentioned above, can be found by one skilled in the art using conventionally known techniques, i.e. dose titration determinations.

An effective coccidiosis-controlling amount of the present quinoxalinedione compounds is ordinarily administered substantially daily to animals and preferably daily during the growth and/or finishing stage of commercial meat-producing animals in a feed lot. Alternatively, the present compounds can be administered to ruminants in the pasture. "Substantially daily" administration of the present quinoxalinedione compounds described herein is meant to encompass dosage schedules, such as, for example, every other day administration or administration 5 or 6 days in each 7-day period, as well as each and every day administration all of which are within the scope of the present invention.

The present quinoxalinedione compounds are conveniently incorporated in a standard feed composition in an appropriate amount to achieve the desired daily dosage. This amount will vary depending upon the amount of feed composition consumed daily by the animal. For example, one or a mixture of two or more of the present quinoxalinedione compounds are effectively incorporated in an animal feed composition at a concentration in the range of from about 50 to about 500 grams per ton of feed (55–550 ppm). The present quinoxalinedione compounds may also be incorporated in a mineral, protein or energy-type feed additive supplement or water supply in an appropriate amount to provide an effective coccidiosis-controlling daily dosage. Standard animal feed formulations, methods of preparing them and methods of uniformly incorporating bioactive materials into feed formulations are well known to one skilled in the art.

For commercial use, it is common to provide a feed additive premix, mineral supplement or concentrate containing one or more of the present quinoxalinedione compounds in a proportion such that a predetermined quantity of the premix is to be added per ton of complete feed, for example, from about 0.1 to about 1000 pounds contains from about 50 to about 500 grams of one or a mixture of the present quinoxalinedione compounds. The feed additive premix or concentrate comprises one or more of the present quinoxalinedione compounds and a physiologically acceptable carrier such as soybean meal or ground corn or other edible feed grade material, mineral mixtures or innocuous diluent, such as, an alcohol, a glycol or molasses, physiologically suitable for the animal at hand. A concentrate may contain from about 0.001 to about 99 percent by weight of one or a mixture of two or more of the present quinoxalinedione compounds in intimate admixture with a suitable adjuvant therefor.

In further embodiments, the method of the present invention contemplates treating or dosing an animal with one of the present novel compositions containing at least one of the present quinoxalinedione compounds as the active ingredient which also can be advantageously employed in combination with one or more additional additives such as, antibiotics, minerals, vitamins or growth promoters employed in animal husbandry.

The animal feeds most generally used in conjunction with this invention are composed of various grain and/or grain mixtures and/or roughage feeds such as hay, cotton seed hulls, rice hulls, silage, or other high fiber feedstuffs commonly fed to meat, egg, milk, and/or wool-producing animals. The feeds for swine or poultry will consist primarily of various grain mixtures plus the usual additaments such as bran meal, soybean meal, cotton seed meal, tankage or alfalfa meals suitable for swine or poultry. Especially preferred animal feeds are poultry feeds.

Examples of physiologically acceptable carriers for premix or concentrate compositions include soybean meal, corn oil, ground corn, ground corn cobs, barley, wheat mineral mixtures containing, e.g. vermiculite or diatomaceous earth, corn gluten meal, corn distillers' solubles or soy flour. The active ingredient will be used in amounts to satisfy the criteria set forth above. This premix or concentrate is then in turn mixed uniformly with a nutritionally sufficient feed for the animal as desired by the grower or the feed mixer. The above-mentioned grains, grain mixtures, roughage feeds, usual additives, carriers and innocuous diluents constitute physiologically acceptable adjuvants for purposes of this invention.

The dosage of a preferred compound, 7-chloro-5-nitro-2(1H),3(4H)-quinoxalinedione, in poultry falls in the range of from about 4 to about 46 mg/kg/day or from about 50 to about 500 grams/ton of feed (55–500 ppm) and preferably in the range of from about 10 to about 20 mg/kg/day or from about 100 to about 225 grams/ton of feed (110–250 ppm). The 7-chloro-5-nitro-2(1H),3(4H)-quinoxalinedione can be uniformly dispersed into commercially available poultry feeds, such as, for example, Chicken Startena brand starter feed and Chicken Growena brand finishing feed both available from The Ralston Purina Company, St. Louis, Mo.

The following examples illustrate the practice of the present invention but, as such, should not be construed as limitations upon the overall scope of the same.

EXAMPLE 1

A fortified complete ration to be fed to broiler chickens during the finishing period which controls coccidiosis in broilers consuming said ration comprises:

| Ingredient | Weight Percent | |
| --- | --- | --- |
| Ground yellow corn | 62.70 | |
| Soybean meal (48.5% protein) | 29.66 | |
| Iodized salt | 0.40 | |
| Microingredients* | 0.50 | |
| Poultry oil | 3.63 | |
| Ground limestone | 0.97 | |
| Dicalcium phosphate (22% Ca; 18.5% P) | 1.84 | |
| DL-Methionine | 0.30 | |
| One or more compounds of Formula I | 100–250 | Grams/ton of ration |
| Calculated Analysis | | |
| Crude protein, % | 20.00 | |
| Metabolizable energy, kcal/kg | 3170 | |
| Ca, % | 0.9 | |
| P, % | 0.7 | |

*Ingredients supplied per kilogram of diet: vitamin A, 6600 IU; vitamin D3, 2200 ICU; menadione dimethylpyrimidinol bisulfite, 2.2 mg; riboflavin 4.4 mg; pantothenic acid, 13.2 mg; niacin, 39.6 mg; choline chloride, 499.4 mg; vitamin B12, 22 ug; ethoxyquin, 0.0125%; manganese, 60 mg; iron, 50 mg; copper, 6 mg; cobalt, 0.198 mg; zinc, 35 mg.

The feed is prepared by dissolving the compound(s) of Formula I in an acceptable but relatively volatile solvent, i.e. methanol, ether, acetone, etc., and thoroughly blending this solution into five pounds of corn meal. The solvent is then allowed to evaporate. The five pounds of corn meal containing the compound(s) of Formula I are then thoroughly blended into 1995 pounds of ration to make one ton of feed.

EXAMPLE 2

A broiler chicken feed described in Example 1 is prepared using 7-chloro-5-nitro-2(1H),3(4H)-quinoxalinedione as the active coccidiosis-controlling agent.

EXAMPLE 3

A fortified complete ration to be fed to turkeys is prepared employing substantially the same procedures described in Example 1 except that a standard turkey feed is used in place of the standard broiler feed. This turkey feed controls coccidiosis in turkeys consuming the feed. The ingredients are listed below:

| Ingredients | Weight percent |
| --- | --- |
| Ground yellow corn | 44.399 |
| Stabilized animal and vegetable fat | 3.0 |
| Dehulled soybean meal | 41.5 |
| Menhaden fish meal | 5.0 |
| Corn distiller's dried grain with solubles | 2.5 |
| Defluorinated phosphate | 2.6 |
| Ground limestone | 0.5 |
| Iodized salt | 0.3 |
| Trace mineral mix* | 0.0617 |
| Vitamin and feed premix** | 0.1393 |

*The following quantities of minerals in milligrams were supplied per kilogram of diet: 250 manganese oxide, 140 zinc oxide, 167 ferric citrate, 20 cupric sulfate, 1 cobalt acetate, 30 potassium iodate, and 9 sodium molybdate.
**The following quantities of vitamin supplements in milligrams were supplied per kilogram of diet: 36.7 vitamin A (300,000 IU/g), 8.3 vitamin $D_3$ (400,000 ICU/g), 25 vitamin E (227 IU/g), 7 menadione sodium bisulfite complex, 1.1 thiamine HCl, 4.4 riboflavin, 11 calcium pantothenate (D), 44 niacin, 1000 choline chloride (50% pure), 10 vitamin B12 (1.32 mg/g), 1.6 folic acid, 55 biotin (1 mg/g in cerelose), 1.1 pyridoxine HCl, and 187.5 ethoxyquin (66% pure).

EXAMPLE 4

A turkey feed described in Example 3 is prepared using 7-chloro-5-nitro-2(1H),3(4H)-quinoxalinedione as the active coccidiosis controlling agent.

EXAMPLE 5

An in vitro coccidiostat screening test was conducted in chicken kidney tissue cultures. Cells were cultured in non-medicated media for 48 hours to establish monolayers. The media in two cultures was removed and replaced with media containing 20 ppm and 0.2 ppm, respectively, of 7-chloro-5-nitro-2(1H),3(4H)-quinoxalinedione. A standard suspension of E. tennella sporozoites was added to the culture media. Three days later observations were made on the growth of the parasite and the condition of the monolayer. Substantially complete control of the E. tennella was achieved at both concentrations with no apparent cytotoxicity to the cell monolayer.

EXAMPLE 6

An in vivo screening test was carried out in chickens to determine the effectiveness of 7-chloro-5-nitro-2(1H),3(4H)-quinoxalinedione as a coccidiostat. Thirteen-day-old white leghorn cockerels were weighed, allotted five to a cage and started on a standard diet. The birds in one cage received feed containing 250 ppm by weight (227 grams/ton) of 7-chloro-5-nitro-2(1H),3(4H)-quinoxalinedione. These birds will be referred to as the treated birds. One day later (when the birds were 14 days old) the treated birds and a non-treated group were infected orally with oocysts of Eimeria tenella (Et) and Eimeria necatrix (En). The challenges were considered very severe. After seven days, the birds were weighed, sacrificed and lesion scored for each species of coccidia. A group of non-infected, non-treated birds was also maintained as a control. The results are listed below.

| Group | Deaths (Dead/Total) | % Survival | Weight Gain (g) | % Gain | Bloody Feces | Lesions En/Et |
| --- | --- | --- | --- | --- | --- | --- |
| Non-infected Control | 0/20 | 100 | 61.8 | 100 | No | No/No |
| Infected Control | 19/20 | 5 | 0.4 | 0 | Yes | Yes/Yes |
| Treated Group | 0/5 | 100 | 54.4 | 88 | Slight | No/Slight |

In similar operations, various compounds of Formula I and mixtures thereof provide control of coccidiosis in animals including poultry.

I claim:

1. A method for controlling coccidiosis in animals which comprises orally administering to said animals an effective coccidiosis-controlling amount of one or more active compounds corresponding to the formula

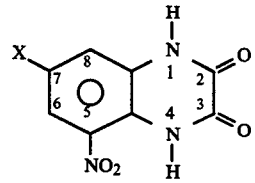

wherein
X represents H, Cl, Br, F, I, $CCl_3$, $CCl_2F$, $CClF_2$, $CHF_2$ or $CF_3$; and
tautomers or physiologically acceptable salts thereof, the effective amount being in the range of from about 0.1 to about 100 mg/kg of body weight of the animal per day.

2. The method of claim 1 wherein the active compound is 7-chloro-5-nitro-2(1H),3(4H)-quinoxalinedione which corresponds to the formula

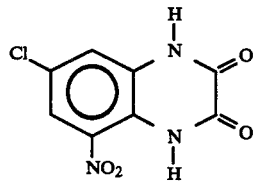

or a tautomer thereof; said animals are poultry; and the active compound is administered orally.

3. The method of claim 2 wherein the poultry are turkeys or broiler chickens.

4. The method of claim 2 wherein the active compound is administered to the poultry at a rate of from about 4 mg/kg body weight/day to about 23 mg/kg body weight/day.

5. The method of claim 2 wherein the active compound is administered to the poultry at a rate of from about 10 mg/kg body weight/day to about 20 mg/kg body weight/day.

6. The method of claim 1 wherein the active compound is administered to the poultry at a rate of from about 0.1 mg/kg body weight/day to about 100 m/kg body weight/day.

7. The method of claim 2 wherein the active compound is administered to the poultry by incorporating the compound into a standard poultry feed in an amount of from about 50 to about 500 grams per ton of feed.

8. The method of claim 2 wherein the active compound is administered to the poultry by incorporating the active compound into a standard poultry feed in an amount of from about 125 to about 225 grams per ton of feed.

9. The method of claim 8 wherein the poultry are turkeys or broiler chickens.

* * * * *